United States Patent [19]

Ahmed

[11] Patent Number: 4,950,440
[45] Date of Patent: * Aug. 21, 1990

[54] PROCESS FOR THE MANUFACTURE OF HIGH FATTY ACID MONOGLYCERIDE MONOSULFATE DETERGENTS

[75] Inventor: Fahim U. Ahmed, Dayton, N.J.

[73] Assignee: Colgate-Palmolive Company, Piscataway, N.J.

[*] Notice: The portion of the term of this patent subsequent to May 23, 2006 has been disclaimed.

[21] Appl. No.: 323,461

[22] Filed: Mar. 14, 1989

Related U.S. Application Data

[63] Continuation-in-part of Ser. No. 96,102, Sep. 14, 1987, Pat. No. 4,832,876.

[51] Int. Cl.$^5$ .......................................... C07C 303/24
[52] U.S. Cl. ...................................... 260/400; 558/32
[58] Field of Search ........................... 260/400; 558/32

[56] References Cited

U.S. PATENT DOCUMENTS

| | | | |
|---|---|---|---|
| 2,006,309 | 6/1935 | Clark | 260/400 |
| 2,130,361 | 9/1938 | Munue | 260/400 |
| 2,163,133 | 6/1939 | Satrauth | 558/32 |
| 2,204,433 | 6/1940 | Muncie et al. | 260/400 |
| 2,235,098 | 3/1941 | Brandt et al. | 260/400 |
| 2,242,979 | 5/1941 | Muncie | 260/400 |
| 2,687,420 | 8/1954 | Brady | 260/400 |
| 2,868,812 | 1/1959 | Gray | 260/400 |
| 2,979,521 | 4/1961 | Gray | 260/400 |
| 3,167,570 | 1/1965 | Bohunek | 260/400 |

FOREIGN PATENT DOCUMENTS 0666206 2/1952 United Kingdom ................ 260/400

*Primary Examiner*—Patrick P. Garvin
*Assistant Examiner*—E. D. Irunski
*Attorney, Agent, or Firm*—Richard Jl. Ancel; Robert C. Sullivan; Murray M. Grill

[57] ABSTRACT

A process for the manufacture of water soluble higher fatty acid monoglyceride monosulfate detergents is described which includes reacting a sulfating agent, such as chlorosulfuric acid, with glycerol in an aprotic organic solvent medium, such as chloroform, to trisulfate the glycerol, reacting the glycerol trisulfuric acid made with a higher fatty acid or a higher fatty acid methyl ester in such a solvent, extracting the reaction mixture with a solvent for the monoglyceride disulfuric acid, such as aqueous lower alkanol, and neutralizing the extracted monoglyceride disulfuric acid with an aqueous neutralizing agent to make the water soluble detergent salt. In a modification of the process the extraction and neutralization operations are effected simultaneously, preferably with a slurry of sodium bicarbonate, as neutralizing agent, in aqueous lower alkanol. In another variation of the process a starting material is glycerol trisulfuric acid, which may be made by processes different from the described glycerol sulfation in aprotic solvent.

The products resulting are of improved quality and of higher detergent content than obtained by prior art processes and the processes are more efficient, requiring only stoichiometric amounts of reagents, reducing formation of sodium sulfate, and improving the yields of detergents.

10 Claims, No Drawings

PROCESS FOR THE MANUFACTURE OF HIGH FATTY ACID MONOGLYCERIDE MONOSULFATE DETERGENTS

This application is a continuation-in-part of my application Ser. No. 07/096,102, filed Sept. 14, 1987, now U.S. Pat. No. 4,832,876.

This invention relates to a process for manufacturing a synthetic organic detergent. More particularly, it relates to a process for making a higher fatty acid monoglyceride monosulfate detergent.

Higher fatty monoglyceride monosulfate detergents, which are of the formula

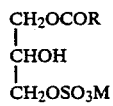

wherein R is a higher fatty alkyl radical of 7 to 17 carbon atoms and M is alkali metal, ammonium, or triethanolamine, are well known and have been employed as mild and effective anionic detergents in shampoos, unbuilt detergent powders, synthetic detergent bars and combination soap-synthetic detergent bars. Such detergents have been manufactured by reacting fatty materials with large excesses of sulfating agents, hydrolyzing, and neutralizing the sulfated monoglycerides that resulted. Also, monoglycerides have been sulfated and then neutralized to produce the desired monoglyceride sulfates. Another process utilizes chloroform as a solvent for a monoester of a polyol (or diol), with chlorosulfuric acid being employed to sulfate the dissolved polyol, after which the sulfuric acid compound made is neutralized with ammonia or other neutralizing agent. In yet another reaction for the production of monoglyceride sulfates a triglyceride is reacted with glycerol trisulfuric acid and a large excess of sulfuric acid, after which the monoglyceride sulfuric acid resulting is neutralized.

While such processes are effective for manufacturing the desired higher fatty acid monoglyceride monosulfate detergents, often the detergent composition resulting includes a substantial proportion of inorganic sulfate byproduct, and therefore is low in active ingredient (A.I.) or detergent content. Practicing the process of the present invention often allows the utilization of approximately stoichiometric proportions of reactants (instead of large excesses, as are sometimes required in other processes), and results in products which are of higher A.I. and lower inorganic sulfate contents, both before and after alcoholic extractions.

Among references found in searches for art which could be relevant to this invention are: U.S. Pat. Nos.: Re. 20,636 (reissue of U.S. Pat. No. 2,023,387); 2,006,309; 2,130,361; 2,163,133; 2,204,433; 2,212,521; 2,235,098; 2,242,979; 2,687,420; 2,868,812; 2,979,521; and 3,167,570; and British Patent Specification No. 666,206. However, such references are not considered to anticipate or make obvious the subject matter of the present application.

In accordance with the present invention, a process for the manufacture of a water soluble salt of a higher fatty acid monoglyceride monosulfuric acid comprises reacting about three molar proportions of a sulfating agent with one molar proportion of glycerol in an aprotic solvent medium so that the glycerol is substantially completely sulfated to the trisulfuric acid thereof, reacting the glycerol trisulfuric acid made, which is dissolved in such solvent, with a higher fatty acid or higher fatty acid lower alcohol ester to produce the corresponding monoglyceride disulfuric acid, extracting the reaction mixture with an aqueous lower alcohol solvent for the monoglyceride disulfuric acid to extract such monoglyceride disulfuric acid, and neutralizing and hydrolyzing the monoglyceride disulfuric acid with aqueous neutralizing agent to make the water soluble salt of higher fatty acid monoglyceride monosulfuric acid.

The following equations illustrate preferred reactions of the present invention.

Stage 1:

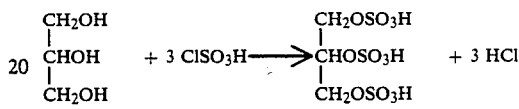

Stage 2:

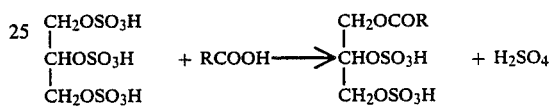

or

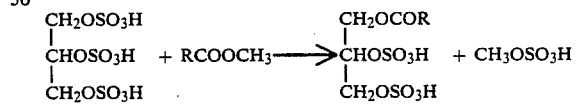

Extraction of Stage 2 Product:

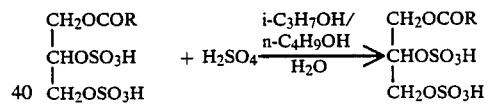

or

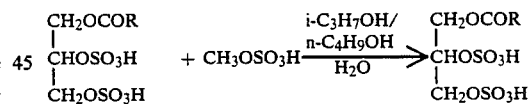

and

Stage 3:

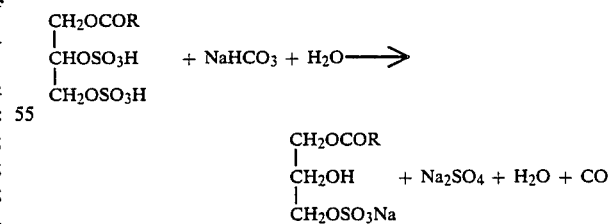

In the Stage 1 reaction glycerol is slowly sulfated with sulfating agent (chlorosulfuric acid) in halogenated solvent (chloroform), preferably at about ambient temperature (but temperatures in the range of 10 to 60° C. are operative). Hydrochloric acid gas, which is generated by the reaction with chlorosulfuric acid, may be vented and diluted in cold water. However, it can be scrubbed and may be reacted with sulfur trioxide gas to produce more chlorosulfuric acid. Alternatively, other sulfating agents can be employed For example, a gaseous mixture of sulfur trioxide and air can be used to partially sulfate the glycerol, preferably at a temperature in the range of 10 to 65° C., e.g., 35 to 65° C., to produce a product of about two degrees of sulfation, which product may be further sulfated to three degrees of sulfation by oleum or other strong form of sulfuric acid. In other forms of the reaction the glycerol trisulfuric acid may be made directly by oleum sulfation of glycerol or by oleum sulfation after sulfuric acid sulfation, with some or all of such sulfations being conducted in an aprotic solvent medium.

Like the Stage 1 reaction, the Stage 2 reaction is carried out in an aprotic solvent, preferably chloroform or ethylene chloride. The glycerol trisulfuric acid employed is preferably that from the Stage 1 reaction (in an aprotic solvent) but glycerol trisulfuric acid made by other processes may also be employed. In the Stage 2 reaction the fatty acid and/or methyl ester is/are preferably dissolved in additional chloroform and is/are added to the glycerol trisulfuric acid, which is also in a chloroform medium, and the condensation reaction occurs, with digestion. The employment of chloroform or other suitable aprotic solvent in Stages 1 and 2 reduces the viscosity of the reaction medium and facilitates smooth agitation and mixing of the various reagents. The chloroform may be recovered from the Stage 2 products by vaporization and condensation during the digestion period or thereafter, or it may be left in the reaction mixture. The extraction, neutralization, and hydrolysis of the detergent diacid are then carried out. The detergent acid may be extracted with a mixture of lower alcohol and water, preferably isopropanol and/or n-butanol and water, and then may be neutralized and hydrolyzed, preferably with a 20 to 35% aqueous sodium hydroxide solution (e.g., about 30% by weight), or neutralization, hydrolysis and extraction may be carried out simultaneously, employing sodium bicarbonate, as the dispersed/dissolved phase, in an aqueous lower alcohol, e.g., n-butanol/isopropanol, medium. Of the two methods it is preferred to utilize the combined neutralization and extraction. Thus, when the "brown acid" mixture of Stage 2 is slowly added to a slurry of sodium bicarbonate in isopropanol or n-butanol, or in mixed isopropanol and n-butanol, with vigorous stirring and maintaining of the pH of the mixture near neutrality (in the range of 6 to 7), the brown color of the acid slowly disappears. The final pH of the mixture, after addition of all the bicarbonate slurry, is adjusted to about 6.5 or 7, preferably 6.5, and the neutralized slurry is heated for about 30 minutes to a temperature of 40 to 60° C., and is then filtered to remove the insoluble inorganic salt (sodium sulfate). Following such filtration the solvent is removed by use of a rotary evaporator and the product is vacuum dried to produce the dried monoglyceride monosulfate, as its sodium salt.

The described synthesis has been illustrated with respect to the higher fatty acyl moiety of the monoglyceride sulfate deriving from any higher fatty acid or its lower alcohol ester, or mixture thereof, but it is preferred that such fatty acid or ester be saturated to avoid any complicating side reactions of olefinic linkages with sulfating agents. For such reasons, when employing mixed fatty acids that are obtained from natural oils or fats, or the lower alcohol esters of such acids, it will be preferred for such to be hydrogenated, such as hydrogenated coconut oil, hydrogenated palm kernel oil, hydrogenated palm oil or hydrogenated tallow, or mixtures thereof, or the corresponding lower alcohol esters of such acids.

The higher fatty acid ester or higher fatty acid lower alcohol ester employed in the invented processes will be one wherein the higher fatty acyl is of 7 to 20 carbon atoms, preferably 8 to 18 carbon atoms and more preferably 10 to 18 or 10 to 14 carbon atoms, e.g., 12 or 14 carbon atoms, and the lower alkyl is of 1 to 3 carbon atoms, preferably being methyl. Such higher fatty acyl moiety is alkanoyl or alkenoyl (of an alkanoic or alkenoic acid) or a mixture thereof, but alkanoyl is preferred, for previously given reasons. Such acids include lauric, myristic, palmitic, oleic and stearic acids, to name a few, and naturally occurring mixtures thereof, which are obtainable from various vegetable and animal oils and fats, including coconut oil, palm kernel oil, palm oil and tallow, and such oils and fats which have been hydrogenated (to decrease or eliminate unsaturation).

The glycerol employed may be synthetic or that which is derived from the splitting of fats and oils, such as occurs in soapmaking. The inventive process is applicable to the production of analogous higher fatty acyl polyol sulfates, such as those of sugars and starches, and polyoxyethylene polyols. However, the invention is considered to be most desirably employed in the manufacturing of monoglyceride monosulfate detergents and, accordingly, this specification and the claims are directed primarily to such processes.

The sulfating agent employed is preferably chlorosulfuric acid (ClSO$_3$H) but other sulfating agents may also be utilized, such as gaseous or liquid sulfur trioxide, oleum, sulfuric acid, fuming sulfuric acid, and mixtures thereof.

The solvents and media for reaction that are employed are preferably organic solvents of a limited polarity, which is preferably like that of chloroform or ethylene chloride. In fact, chloroform is the preferred solvent but other lower boiling aprotic solvents, which are usually halogenated lower hydrocarbons of 1 to 6 carbon atoms, preferably aliphatic halogenated hydrocarbons of 1 to 4 carbon atoms, are also useful. In such compounds the halogen may be chlorine, fluorine and/or bromine, with chlorine and bromine being preferred. Among such solvents may be mentioned carbon tetrachloride, trichloroethylene, ethylene dichlride, $CH_2Cl_2$ and the various fluorinated hydrocarbons and chlorofluorinated hydrocarbons known as Freons®, which include Freons or Propellents 11, 12, 21, 22 113 and 114, singly or in mixtures. In some instances the corresponding hydrocarbons are also useful, as in mixtures with halogenated solvents. Carbon disulfide is also operative. It is often desirable that such solvents be comparatively low boiling so that they may be easily evaporated from the reaction mixture after completion of digestion and before neutralization of the detergent acid. For example, atmospheric boiling points for such solvents are usually in the range of about 40 to 90° C., e.g., 60 to 80° C. The reaction may be conducted at elevated pressure, as up to 5 kg./sq. cm., and solvent may be removed under vacuum conditions, but operations and reactions at atmospheric pressure are preferred.

The extracting medium or solvent utilized, which helps to separate the monoglyceride disulfuric acid made in the sulfation reaction from sulfuric acid or the monoalkyl ester of sulfuric acid (which results from reactions utilizing alkyl ester of higher fatty acid in the condensation-digestion step), is preferably an aqueous alcoholic medium in which the alcohol is a lower alkanol of 1 to 4 carbon atoms, preferably isopropyl alcohol or normal butyl alcohol or a mixture thereof, but isobutanol, n-propanol and other such mixtures are also operative.

The neutralizing agent is an aqueous solution of an alkali metal (sodium and/or potassium) hydroxide, an alkali metal carbonate, an alkali metal bicarbonate, ammonium hydroxide, ammonium carbonate, ammonium bicarbonate, amines, such as triethanolamine, amine hydroxides, such as triethanolamine hydroxide, or a mixture of a plurality thereof, with sodium hydroxide, sodium bicarbonate and sodium carbonate being the preferred neutralizing agents for making sodium monoglyceride monosulfate detergents according to the process of this invention.

In some instances the extraction and neutralization/hydrolysis operations may be conducted simultaneously, in which cases it is preferable to employ a slurry of sodium bicarbonate neutralizing agent in an aqueous lower alcoholic medium. After manufacture of the detergent salt by the method described and with the reagents mentioned, a further extraction may be effected, wherein any inorganic salt, such as sodium sulfate, which might remain with the desired detergent salt, may be separated from it by further extraction with a lower alcohol or an aqueous solution of such lower alcohol of 1 to 3 or 4 carbon atoms, but such extra extraction is not needed.

The proportions of sulfating agent and glycerol will be equivalent proportions, which normally will include three molar proportions of sulfating agent and one molar proportion of glycerol. It may sometimes be desirable to utilize a small excess of sulfating agent, such as up to 3.2 moles thereof per mole of glycerol. If the sulfating agent is to be sulfur trioxide, trisulfation of the glycerol may not be obtainable and so a greater excess of sulfur trioxide may be employed and a second stage of sulfation may be desirable, such as that effected by a stronger sulfating agent, e.g., oleum. However, when chlorosulfuric acid is employed stoichiometric proportions may be utilized (3:1).

The glycerol employed will be dissolved in chloroform or other suitable solvent, (with the weight of chloroform being from equal to three times that of glycerol, preferably about twice the weight of glycerol). The reaction temperature will most preferably be held to less than 25 or 30° C. However, such temperature range may be 10 to 60° C., preferably 15 or 20 to 50 or 40° C., and in some instances may be as low as 0° C., and the reaction will still proceed satisfactorily. After the completion of the sulfation reaction, which normally will take from 30 minutes to five hours, the glycerol trisulfuric acid is condensed with higher fatty acid or monoalkyl ester of such higher fatty acid. Such condensation reaction, which may sometimes be referred to as a digestion step, is carried out using equimolar proportions of glycerol trisulfuric acid and fatty acid or fatty acid methyl (or other lower alkyl) ester. Variations from such equimolar proportions may be ±5 or ±10% under particular circumstances, but it is preferred that equimolar proportions be used. During the condensation or digestion reaction additional chloroform or other solvent may be employed, with the total weight of such solvent normally being up to four times the total of the weights of glycerol trisulfuric acid and higher fatty acid or higher fatty acid lower alkyl ester. The temperature of the reaction should be in the range of 20 to 80° C., preferably 30 to 60° C. and more preferably 40 to 55° C.

In the extraction step, which follows next, a suitable aqueous-organic solvent is employed, normally with from one part of water to two to four parts of solvent. The solvent is desirably a lower alkanol of one to four carbon atoms per mole, preferably n-butanol or isopropanol or a mixture thereof, such as one of weight ratio in the range of 1:4 to 4:1. The temperature of the extraction is desirably held in the 10 to 60° C. range, preferably 25 or 30 to 50° C.

Subsequent to extraction which removes the monoglyceride disulfuric acid from the sulfuric acid or monoalkyl ester of sulfuric acid, or concurrently therewith, the monoglyceride disulfuric acid is hydrolyzed and neutralized with sodium hydroxide, sodium bicarbonate or other suitable neutralizing agent, which agents were previously listed, to produce the desired salt. In the neutralization reaction the water present hydrolyzes the sulfuric acid moiety joined to the central carbon of the glyceryl nucleus, converting it to hydroxyl, while also converting the monoglyceride disulfuric acid to the desired monoglyceride monosulfate salt. Any byproduct sodium sulfate present may be removed by alcoholic extraction and any water or alcohol still present with the desired detergent salt may be evaporated, or may be left with the detergent salt as solvent(s) for it, if desired.

Alternative to the sequential extraction and neutralization steps is a combined extraction-neutralization operation. In such an operation the preferred neutralizing agent will be sodium bicarbonate or sodium carbonate in an aqueous alcoholic medium. In the neutralization reactions it is desirable to employ a stoichiometric proportion of the neutralizing agent, but sometimes slight excesses, such as 10%, may be used. The amount of water present in the portion of the combined extraction and neutralizing agent will be at least a hydrolyzing proportion and the alcohol content will be ¼ to 4 times the water content. The combined extraction and neutralizing/hydrolyzing medium will normally be maintained at a temperature in the range of 10 to 60° C. and will be stirred continuously and preferably vigorously during the extraction-neutralization operation, with the pH thereof being maintained in the range of 6.0 to 7.0 and normally being about 6.5 at the conclusion of the neutralization reaction, at which point the desired monoglyceride monosulfate detergent will have been produced. Any insoluble inorganic salt, such as sodium sulfate byproduct, may be removed from the detergent by filtration and any lower alcohol and any chloroform remaining may be removed by vaporization. If further purification of the detergent salt is desired, it may be carried out by further alcoholic extraction and filtration of the insoluble salt, but it is an advantage of the invention that such additional extraction-filtration operation is not necessary.

The following examples illustrate the invention but do not limit it. Unless otherwise indicated, all parts and percentages in the examples, specification and claims are by weight and all temperatures are in °C.

EXAMPLE 1

(Synthesis of Sodium Hyrogenated Coco Acids Monoglyceride Monosulfate)

Chlorosulfuric acid (93.2 g., 0.8 mole) is dissolved in 100 ml. of chloroform, and such solution is added dropwise to glycerol (23.0 g., 0.25 mole), which is in a one-liter three-necked flask equipped with a mechanical stirrer, a dropping funnel, a thermometer and a pressure outlet, connected to an oil bubbler. The flask is maintained externally cooled by an ice bath so the reaction temperature during the period when the chlorosulfuric acid is added to glycerine can be maintained below 30° C. The chlorosulfuric acid is added dropwise to the glycerol with vigorous stirring over a period of about 0.5 hour, after which the stirring of the reaction mixture is continued, at room temperature, without addition of more chlorosulfuric acid, for about another half hour to expel all gaseous hydrogen chloride. The reaction mix is viscous and slightly brownish in color.

To the glycerol trisulfuric acid made by the previously described reaction, there is added hydrogenated coconut oil fatty acid (51.4 g., 0.25 mole), in solution in 100 ml. of chloroform. The addition is slow and the temperature of the reaction mixture gradually increases to about 40° C. The reaction mixture is then heated and maintained at about 65° C. by a hot water bath for about 1.5 hours, and about 170 ml. of chloroform are recovered by vaporization and condensation.

The viscous reaction mix resulting is cooled by an ice bath to 10° C. and a mixture of 700 g. of ice and 700 ml. of n-butanol is slowly introduced into the reaction flask with stirring. The liquid mixture resulting is stirred for an additional half hour, while being kept cool on an ice bath. The upper alcoholic layer separates and in it there is contained the monoglyceride disulfuric acid resulting from reaction of the higher fatty acid and glycerol trisulfuric acid. The aqueous lower layer is extracted with two 100 ml. portions of n-butanol and the combined alcohol extracts are washed with 200 ml. of water. The washed alcohol extract is cooled in an ice bath and is slowly neutralized (and hydrolyzed) with aqueous sodium hydroxide (30% concentration) to a pH of 6.5.

The solvent is removed from the neutralized and hydrolyzed mixture by a rotary evaporator. The remaining material is stirred with 500 ml. of acetone and is filtered (the sodium coco monoglyceride monosulfate is insoluble in acetone), after which any solvent present is removed by subjection of the filtered out material to vacuum (vacuum pumping).

The product obtained is analyzed by cationic titration with benzethonium chloride, using methylene blue as the indicator, and is found to be 93% active detergent salt. The yield of product is 82.4 g., which corresponds to a yield of 85%, based on the product, or 79%, based on the active detergent content thereof.

EXAMPLE 2

(Synthesis of Sodium Hydrogenated Palm Kernel Acids Monoglyceride Monosulfate)

Chlorosulfuric acid (93.2 g., 0.8 mole) is dissolved in 50 ml. of chloroform and such solution is added dropwise to a cold (10° C.) dispersion of glycerol (23.0 g., 0.25 mole) in 50 ml. of chloroform over a period of 0.5 hour. The hydrogen chloride evolved is vented. The semi-solid material produced is stirred at ambient temperature for about 0.5 hr. to expel the remaining gaseous hydrogen chloride.

Hydrogenated palm kernel oil fatty acid methyl ester (57.7 g., 0.25 mole) is dissolved in 100 ml. of chloroform and is slowly added to the glycerol trisulfuric acid previously made. The solution resulting is heated to a temperature of 63°–65° C. for two hours, and chloroform is vaporized off and recovered. The viscous material resulting is cooled on an ice bath and 600 ml. of n-butanol and 700 g. of ice are slowly added to it. Such mixture is stirred for 0.5 hr. and an upper alcohol layer that is formed is separated from a lower aqueous layer. The lower layer is extracted with two 150 ml. portions of n-butanol, at room temperature. The alcohol extracts are combined and the combined extract is washed with 300 ml. of water.

The washed alcohol solution of monoglyceride disulfuric acid is then neutralized with aqueous sodium hydroxide solution to a pH of 6.5. The solvent is removed by rotary evaporation and 123.2 g. of material remain. This material is stirred with 600 ml. of acetone, filtered and vacuum dried, yielding 83 g. of solid product, which analyzes to be 67.6% of active detergent salt. Thus, the yield is 57%.

EXAMPLE 3

(Synthesis of Sodium Hyrogenated Palm Acids Monoglyceride Monosulfate)

Chlorosulfuric acid (384.5 g., 3.3 moles) is dissolved in 100 ml. of chloroform. Glycerol (92.1 g., 1 mole) is added slowly, over a period of 0.5 hr., to the stirred solution of chlorosulfuric acid in chloroform, which is in a two liter, three-necked, round bottom flask, while maintaining the reaction mixture at a temperature of less than 30° C. by means of an ice bath. Hydrogen chloride is evolved during the reaction and is vented through a bubbler into ice cold water. Subsequently, the viscous product resulting (glycerol trisulfuric acid) is stirred for an additional 0.5 hour to remove any remaining hydrogen chloride.

Hydrogenated palm oil acid (273.6 g., 1 mole) is partially dissolved in 300 ml. of chloroform and the solution-dispersion resulting is slowly added to the glycerol trisulfuric acid previously made. An additional 50 ml. of chloroform are added and the reaction mixture is heated and refluxed for two hours, after which it is cooled and transferred to a separatory funnel. The desired reaction product in the separatory funnel is hydrogenated palm acid monoglyceride disulfuric acid.

A slurry of 460 g. of sodium bicarbonate, 1500 ml. of isopropanol and 600 ml. of water is made and is kept cold, at 10° C., on an ice bath. A pH electrode, which is connected to a pH meter, is inserted into the bicarbonate slurry so that the pH may be monitored during neutralization. The hydrogenated palm acid monoglyceride disulfuric acid is slowly introduced into the aqueous alcoholic sodium bicarbonate slurry in such manner that the pH is maintained about neutral, in the range of 6.5 to 7.5, although in some instances the range of 6.0 to 7.0 or 7.5 may be used. At the completion of the neutralization of the monoglyderide disulfuric acid the product becomes thick, so 500 ml. of n-butanol are added. The mixture is heated to 60° C., to dissolve all the organic material, and another 500 ml. of isopropanol are added. The mix is then treated with charcoal to improve its color and is cooled to room temperature, at which some detergent salt precipitates, which is filtered out. The filtrate is then cooled to ambient temperature and is concentrated to a solid, after which it is combined with the filtered out product. The combined solids are then stirred in 1500 ml. of acetone, using a mechanical stirrer, and are filtered. A solid white material is thus obtained and is vacuum pumped overnight, powdered, and again subjected to vacuum overnight. The total yield of solid is 386 g., and the active detergent content thereof is found by analysis to be 85.3%. The yield is 76.6%.

EXAMPLE 4

(Syntheses of Various Monoglyceride Monosulfates)

Following the procedure of Example 1, sodium (unhydrogenated) coco acids monoglyceride monosulfate is made, with the sole change in the process being in the employment of a slightly different weight of coco fatty acids due to the slight change in molecular weight (although the molar proportion is the same). The product made is sodium coco monoglyceride monosulfate and the purity and yield are essentially the same as those for the product of Example 1. Similarly, sodium unhydrogenated palm kernel acids monoglyceride monosulfate and sodium unhydrogenated palm acids monoglyceride monosulfate are made, using the same weights of the reactants, except for the fatty acids, wherein the same molar proportions are employed. In the same manner the hydrogenated and non-hydrogenated monoglyceride monosulfates of animal fat acids, such as tallow acids, are made and in some instances blends of acids from tallow with acids from various mentioned vegetable oils, and others, are employed instead.

The procedure of Example 2 is followed, utilizing the fatty acid methyl esters derived from coconut oil, hydrogenated coconut oil, palm kernel oil, palm oil, hydrogenated palm oil, tallow and hydrogenated tallow, and the results are similar. Of course, the reagent weights will differ but the moles are equal.

The process of Example 3, in which a combined neutralization, extraction and hydrolysis is effected, is carried out with the various mentioned fatty acids, hydrogenated fatty acids, fatty acid lower alkyl (methyl) esters and hydrogenated fatty acid lower alkyl (methyl) esters, and the corresponding products are obtained in good yields and purities.

Of course, in the modifications of the basic three examples given above it is sometimes desirable to employ more or less solvent or somewhat different proportions of the reagents to obtain maximum yields and greater purities, but it is considered that such modifications of the invented processes are within the abilities of those skilled in the art who have the present teachings before them.

When the processes of the above examples are repeated, using other sulfating agents to make the glycerol trisulfuric acid, such as oleum, sulfur trioxide, followed by oleum, or concentrated sulfuric acid, followed by oleum, and employing other aprotic halogenated lower hydrocarbon solvents, including methylene chloride, Propellent 11, and carbon tetrachloride, glycerol trisulfuric acid is satisfactorily made. Such is also the result when either or both of the glycerol and sulfating agent is/are dissolved in aprotic solvent, so long as the sulfation reaction is conducted in such a solvent medium. When the glycerol trisulfuric acid so made is then reacted with higher fatty acids of 8 to 18 carbon atoms, followed by extraction of the higher fatty acids monoglyceride disulfuric acid made with other lower alkanol solvent, such as n-propanol, isobutanol or tert. butanol, or a mixture thereof, and followed by neutralization with sodium carbonate, ammonium hydroxide, triethanolamine, potassium hydroxide or potassium bicarbonate, or a mixture thereof, and hydrolysis, the desired monoglyceride monosulfate detergent results. Similar good results are obtained when the neutralizing agent (preferably sodium bicarbonate), extracting alcohol and water are employed together to extract, neutralize and hydrolyze in a single step.

EXAMPLE 5

(Syntheses of Various Monoglyceride Monosulfates from Glycerol Trisulfuric Acid and Higher Fatty Acids and/or Higher Fatty Acid Lower Alcohol Esters)

The procedures of Examples 1–4 are repeated but the glycerol trisulfuric acid employed is made by different processes, such as those of U.S. Pat. No. 2,979,521, Examples IV, VI and VII. Otherwise, the reactions are those of present Examples 1–4, employing the same solvents, and other conditions, and the products resulting are the same water soluble salts of higher fatty monoglyceride monosulfuric acid, in the same good yields and purities.

In the variations of the manufacturing methods described in Examples 4 and 5 the proportions of materials and the reaction conditions, such as temperatures, times and pressures, may be changed within the limits set forth in the specification, and the reactions and separations will proceed as described and the products will be obtained in similar good yields and high active ingredient contents.

The invention has been described with respect to various illustrations and embodiments thereof but is not to be limited to these because it will be evident that one of skill in the art, with the present specification before him/her will be able to utilize various substitutes and equivalents without departing from the invention.

What is claimed is:

1. A process for the manufacture of a water soluble salt of a higher fatty acid monoglyceride monosulfuric acid which comprises reacting about three molar proportions of a sulfating agent with one molar proportion of glycerol in a low boiling, aprotic solvent, so that the glycerol is sulfated to the trisulfuric acid thereof, reacting the glycerol trisulfuric acid made with a higher fatty acid or higher fatty acid lower alkanol ester in such a solvent to produce higher fatty acid monoglyceride disulfuric acid, extracting the reaction mixture resulting with an aqueous-organic solvent for the monoglyceride disulfuric acid produced, and neutralizing and hydrolyzing such extracted monoglyceride disulfuric acid with an aqueous neutralizing agent to produce the water soluble salt of higher fatty acid monoglyceride monosulfuric acid.

2. A process according to claim 1 wherein the higher fatty acid monoglyceride monosulfuric acid is one wherein the higher fatty acyl moiety is of 7 to 20 carbon atoms and is alkanoyl or alkenoyl or a mixture thereof, the aprotic solvent for the glycerol is a halogenated lower hydrocarbon, which is at a temperature in the range of 10 to 60° C., during sulfation of the glycerol, the higher fatty acid or higher fatty acid lower alkanol ester is an alkanoic or alkenoic acid or methyl ester of such an acid of 7 to 20 carbon atoms in the acid, the sulfating agent is chlorosulfuric acid, sulfuric acid, oleum and/or sulfur trioxide, the reaction of the glycerol trisulfuric acid and higher fatty acid or ester to produce monoglyceride disulfuric acid is conducted at a temperature in the range of 20 to 80° C., the solvent for the monoglyceride disulfuric acid is an aqueous lower alkanol of 1 to 4 carbon atoms, and the neutralizing agent is an aqueous solution of an alkali metal hydroxide, an alkali metal carbonate, an alkali metal bicarbonate, ammonium hydroxide, ammonium carbonate, ammonium bicarbonate, triethanolamine or triethanolamine hydroxide, or a plurality thereof.

3. A process according to claim 2 wherein the higher fatty acid monoglyceride monosulfuric acid is of a higher fatty acids monoglyceride wherein the higher fatty moiety is cocoyl or palm kerneloyl, the organic aprotic solvent is chloroform, the temperature of the reaction to produce glycerol trisulfuric acid is about ambient, the glycerol trisulfuric acid is reacted with a coco or palm kernel fatty acid, or coco or palm kernel fatty acid methyl ester at a temperature in the range of 35 to 65° C., the solvent for such reaction includes additional chloroform, the extraction of the reaction mixture is with an n-butanol-water mixture and the neutralization and hydrolysis of the extracted monoglyceride disulfuric acid is by sodium hydroxide, sodium carbonate or sodium bicarbonate, or a plurality thereof.

4. A process according to claim 3 wherein the higher fatty moiety of the fatty monoglyceride monosulfuric acid is hydrogenated cocoyl, the reaction of the glycerol trisulfuric acid is with hydrogenated coco fatty acids, the extraction of the reaction mixture is with an n-butanol-water mixture in which the weight of water is about equal to that of n-butanol, and the neutralization and hydrolysis of the monoglyceride disulfuric acid is with an aqueous solution of sodium hydroxide.

5. A process according to claim 3 wherein the higher fatty moiety of the fatty monoglyceride monosulfuric acid is hydrogenated palm kerneloyl, the reaction of the glycerol trisulfuric acid is with hydrogenated palm kerneloyl fatty acid, the extraction of the reaction mixture is with an n-butanol-water mixture in which the weight of water is about equal to that of n-butanol, and the neutralization and hydrolysis of the monoglyceride disulfuric acid is with an aqueous solution of sodium hydroxide.

6. A process according to claim 1 wherein the extraction, neutralization and hydrolysis are carried out simultaneously, utilizing a slurry of sodium bicarbonate, as neutralizing agent, in an aqueous lower alcohol medium, which is stirred vigorously while the pH thereof is maintained in the range of 6.0 to 7.0, insoluble inorganic salt is removed, after such extraction, neutralization and hydrolysis, by filtration, and water, lower alkanol and the organic solvent are removed by evaporation, resulting in the production of sodium higher monoglyceride monosulfate in improved yield.

7. A process according to claim 3 wherein the higher fatty moiety of the fatty monoglyceride monosulfuric acid is hydrogenated cocoyl, the reaction of the glycerol trisulfuric acid made is with hydrogenated coco fatty acid, the extraction, neutralization and hydrolysis are carried out simultaneously, utilizing a slurry of sodium bicarbonate, as neutralizing agent, in the aqueous lower alcoholic medium, which is stirred vigorously while the pH thereof is maintained in the range of 6.0 to 7.0, insoluble inorganic salt is removed by filtration after extraction, neutralization and hydrolysis, and water, lower alkanol and chloroform are removed by evaporation, resulting in the production of sodium hydrogenated cocoyl monoglyceride monosulfate in improved yield.

8. A process according to claim 3 wherein the higher fatty moiety of the fatty monoglyceride monosulfuric acid is hydrogenated palm kerneloyl, the reaction of the glycerol trisulfuric acid made is with hydrogenated palm kernel fatty acid, the extraction, neutralization and hydrolysis are carried out simultaneously, utilizing a slurry of sodium bicarbonate, as neutralizing agent, in the aqueous lower alcoholic medium, which is stirred vigorously while the pH thereof is maintained in the range of 6.0 to 7.0, insoluble inorganic salt is removed by filtration after extraction, netralization and hydrolysis, and water, lower alkanol and chloroform are removed by evaporation, resulting in the production of sodium hydrogenated palm kerneloyl monoglyceride monosulfate in improved yield.

9. A process for the manufacture of a water soluble salt of a higher fatty acid monoglyceride monosulfuric acid which comprises reacting about one molar proportion of glycerol trisulfuric acid with a molar proportion of a higher fatty acid or higher fatty acid lower alkanol ester in an aprotic solvent to produce higher fatty acid monoglyceride disulfuric acid, extracting the reaction mixture resulting with an aqueous-organic solvent for the monoglyceride disulfuric acid produced, and neutralizing and hydrolyzing such extracted monoglyceride disulfuric acid with an aqueous neutralizing agent to produce the water soluble salt of higher fatty acid monoglyceride monosulfuric acid.

10. A process according to claim 9 wherein the higher fatty acid monoglyceride monosulfuric acid is one wherein the higher fatty acyl moiety is of 7 to 20 carbon atoms and is alkanoyl or alkenoyl or a mixture thereof, the aprotic solvent is a halogenated lower hydrocarbon, the higher fatty acid or higher fatty acid lower alkanol ester is an alkanoic or alkenoic acid or methyl ester of such an acid of 7 to 20 carbon atoms in the acid, the reaction of the glycerol trisulfuric acid and higher fatty acid or ester to produce monoglyceride disulfuric acid is conducted at a temperature in the range of 20 to 80° C., the solvent for the monoglyceride disulfuric acid is an aqueous lower alkanol of 1 to 4 carbon atoms, and the neutralizing agent is an aqueous solution of an alkali metal hydroxide, an alkali metal carbonate, an alkali metal bicarbonate, ammonium hydroxide, ammonium carbonate, ammonium bicarbonate, triethanolamine or triethanolamine hydroxide, or a plurality thereof.

* * * * *